(12) United States Patent
Plauché et al.

(10) Patent No.: US 7,137,973 B2
(45) Date of Patent: Nov. 21, 2006

(54) POST TUMESCENT LIPOSUCTION ABSORPTION PAD GARMENTS

(75) Inventors: Susan H. Plauché, Knoxville, TN (US); Holly Shaw, Knoxville, TN (US)

(73) Assignee: Evanton Solutions, LLC, Knoxville, TN (US)

( * ) Notice: Subject to any disclaimer, the term of this patent is extended or adjusted under 35 U.S.C. 154(b) by 0 days.

(21) Appl. No.: 10/946,086

(22) Filed: Sep. 22, 2004

(65) Prior Publication Data
US 2006/0064067 A1   Mar. 23, 2006

(51) Int. Cl.
*A61F 13/15* (2006.01)
*A61F 13/00* (2006.01)
*A61F 15/00* (2006.01)
*A61B 19/00* (2006.01)

(52) U.S. Cl. .................. 604/397; 604/358; 602/79; 602/58

(58) Field of Classification Search .............. 604/358, 604/385.14, 357, 398, 397; 602/53, 79, 58
See application file for complete search history.

(56) References Cited

U.S. PATENT DOCUMENTS

| | | | | | |
|---|---|---|---|---|---|
| 808,433 | A | * | 12/1905 | Cartledge | 450/116 |
| 2,560,712 | A | * | 7/1951 | Bell | 602/60 |
| 2,579,275 | A | * | 12/1951 | Schworm, Jr. | 604/394 |
| 2,596,275 | A | * | 5/1952 | Muller | 602/79 |
| 2,698,620 | A | * | 1/1955 | Larkins | 604/394 |
| 2,856,931 | A | * | 10/1958 | Teet | 450/107 |
| 2,926,665 | A | * | 3/1960 | Seese | 602/42 |
| 3,125,093 | A | * | 3/1964 | Hutchins | 604/397 |
| 3,442,270 | A | * | 5/1969 | Steinman | 602/79 |
| 3,489,149 | A | * | 1/1970 | Larson | 604/394 |
| 3,888,245 | A | * | 6/1975 | Bernston et al. | 602/19 |
| 4,205,674 | A | * | 6/1980 | Porat et al. | 602/58 |
| 4,291,427 | A | * | 9/1981 | Rhea | 441/120 |
| 4,345,591 | A | * | 8/1982 | Hedgren | 602/53 |
| 4,507,801 | A | * | 4/1985 | Kavanagh et al. | 2/462 |
| 4,802,469 | A | * | 2/1989 | Gollestani | 128/98.1 |
| 4,820,296 | A | * | 4/1989 | Masliyah | 604/385.03 |
| 5,007,412 | A | * | 4/1991 | DeWall | 602/19 |
| 5,069,672 | A | * | 12/1991 | Wippler et al. | 604/385.14 |
| 5,300,058 | A | * | 4/1994 | Goulait et al. | 604/391 |
| 5,456,660 | A | * | 10/1995 | Reich et al. | 602/79 |
| 5,533,963 | A | * | 7/1996 | Hall | 602/75 |
| 5,556,375 | A | * | 9/1996 | Ewall | 602/58 |
| 5,810,699 | A | * | 9/1998 | Nadeau | 182/105 |
| 5,843,025 | A | * | 12/1998 | Shaari | 602/53 |
| 5,950,238 | A | * | 9/1999 | Klein | 2/69 |
| 5,976,099 | A | * | 11/1999 | Kellogg | 602/23 |
| 5,977,428 | A | * | 11/1999 | Bozigian et al. | 602/48 |
| 5,994,612 | A | * | 11/1999 | Watkins | 602/41 |
| 6,018,092 | A | * | 1/2000 | Dunshee | 602/54 |
| 6,158,429 | A | * | 12/2000 | Gardner et al. | 128/201.25 |
| 6,258,051 | B1 | * | 7/2001 | Shesol et al. | 602/79 |

(Continued)

*Primary Examiner*—Tatyana Zalukaeva
*Assistant Examiner*—Paula L. Craig
(74) *Attorney, Agent, or Firm*—Knox Patents; Thomas A. Kulaga

(57) ABSTRACT

Garments that are an absorption pad holding system used during post tumescent liposuction drainage recovery. These garments with rows of inside pockets will secure retail maxi pads and/or medical pads in a, but not limited to, stretchable, breathable, leak proof and washable material. These user friendly garments after being filled with pads, can be easily wrapped around various parts of the body. The garment can be easily adjusted with the Velcro closure.

19 Claims, 8 Drawing Sheets

U.S. PATENT DOCUMENTS

| | | | |
|---|---|---|---|
| 6,269,820 B1 * | 8/2001 | Bays | 128/898 |
| 6,283,124 B1 * | 9/2001 | Schleuning et al. | 128/845 |
| 6,292,950 B1 * | 9/2001 | Mentone | 2/236 |
| 6,585,673 B1 * | 7/2003 | Bass | 602/60 |
| 6,593,508 B1 * | 7/2003 | Harder | 602/56 |
| 6,659,970 B1 * | 12/2003 | Woodworth et al. | 602/3 |
| 6,763,835 B1 * | 7/2004 | Grove et al. | 128/857 |
| 6,989,005 B1 * | 1/2006 | LaVon et al. | 604/385.14 |
| 2001/0025166 A1 * | 9/2001 | Campbell | 604/397 |

* cited by examiner

POST TUMESCENT LIPOSUCTION ABSORPTION PAD GARMENTS

FIELD OF THE INVENTION

The present invention relates to . . . An absorption pad support garment and, more particularly, to . . . secure and keep in place retail disposable feminine maxi pads and/or medical pads for collection of drainage fluid.

BACKGROUND OF THE INVENTION

Immediately after tumescent liposuction, the patient experiences a tremendous amount of blood tinged tumescent fluid drainage. In order to absorb the fluid, various types of absorption pads are used post-operatively, including medical pads and/or over the counter feminine maxi-pads. The problem arises when a patient tries to change these pads on the wound site when saturated with tumescent fluid drainage, and then apply a compression garment.

The amount of drainage requires the absorption pads to be changed by the patient frequently during the first few days after tumescent liposuction. The process of removing and re-applying new absorption pad is time consuming, cumbersome, painful, frustrating, and difficult task for the patient to do without assistance. Changing pads entails removing elastized material and the painful removal of tape, which secures flat absorption and/or individual maxi pads to the skin. Re-applying the new pads entails manually holding pads in place over the leaking tumescent wounds while securing pads with medical tape to the skin. Finally, the last step is wrapping or putting on elastized material to further secure absorption pads in place. This is an inefficient and daunting task for any recuperating patient.

U.S. Pat. No. 6,283,124, which was issued to Jeff Scheuning and Marc Sperberg discloses a Versatile Compression Garment including, in combination, a form-fitting garment portion and one or more compression pads. One or more compression pads are disposed in a receiving pouch or pouches located on the interior surface of the garment. The position of the compression pad or pads is such that they overlie the portion of a body which is desired to be compressed when the form-fitting garment is donned. When performing the surgical procedure of suction lipoplasty it is desirable to compress the surgical site postoperatively in order to minimize swelling. Following removal of the liposuction cannula the operative site is closed and covered with a surgical bandage. The garment is then fitted onto the body with the compression pad overlying the surgical area. In another embodiment an adhesive surface on the compression pad is adapted to releasably adhere to a portion of the inner body-facing surface of the garment. The ability to move and reposition of the compression pads on the interior surface of a form-fitting garment so as to overlie the surgical site provides a versatile compression garment.

U.S. Pat. No. 6,585,673 which was issued to Andrea Bass, discloses a Pressure binder and pack positioner which can also be used as a hot/cold pack positioner. More specifically, the present invention is primarily intended for bodily use by being positioned either over or under a garment to provide comfort support to various selected body parts and also to aid in the faster recovery of various injured body parts. An elasticized pressure binder and pack position comprises a pocket, a pair of elongated elasticized straps, and a pair of elongated extension straps. The pocket has three closed ends and one open end. The open end can be closed by means for closing. The pair of elongated elasticized straps is attached to and extending from one of the three closed ends. There are a pair of hook portions of a hook and loop type fastener structure on the side of the pocket. There is a loop portion of the hook and loop fastener structure at the end of each of the pair of elongated elasticized straps. One side of each of the pair of elongated extension straps is a loop portion of the hook and loop fastener structure. The other side of each of the pair of elongated extension straps is a hook portion of the hook and loop fastener structure.

Each of these prior arts, discloses a kind of Holder, Support and Compression garment, however, none of them accommodates the convenient use of over the counter Maxi pads and addresses the Tumescent Liposuction drainage.

Such a garment is lacking in the prior art.

It is an object of this invention to provide an improved method of collecting post liposuction drainage fluid.

It is another object of the invention to allow the consumer an easy way to secure maxi pads and/or medical pads to the garment.

SUMMARY OF THE INVENTION

In accordance with the present invention, there is provided . . . garments that are an absorption pad holding system used during post tumescent liposuction drainage recovery. These garments with rows of inside pockets will secure retail maxi pads and/or medical pads in a, but not limited to, stretchable, breathable, leak proof and washable material. These user friendly garments after being filled with absorption pads can be easily wrapped around various parts of the body. The garment can be easily adjusted with the Velcro closure.

BRIEF DESCRIPTION OF THE DRAWINGS

A complete understanding of the present invention may be obtained by reference to the accompanying drawings, when considered in conjunction with the subsequent, detailed description, in which.

For purposes of clarity and brevity, like elements and components will bear the same designations and numbering throughout the FIGURES.

DESCRIPTION OF THE PREFERRED EMBODIMENT

Figure 1:
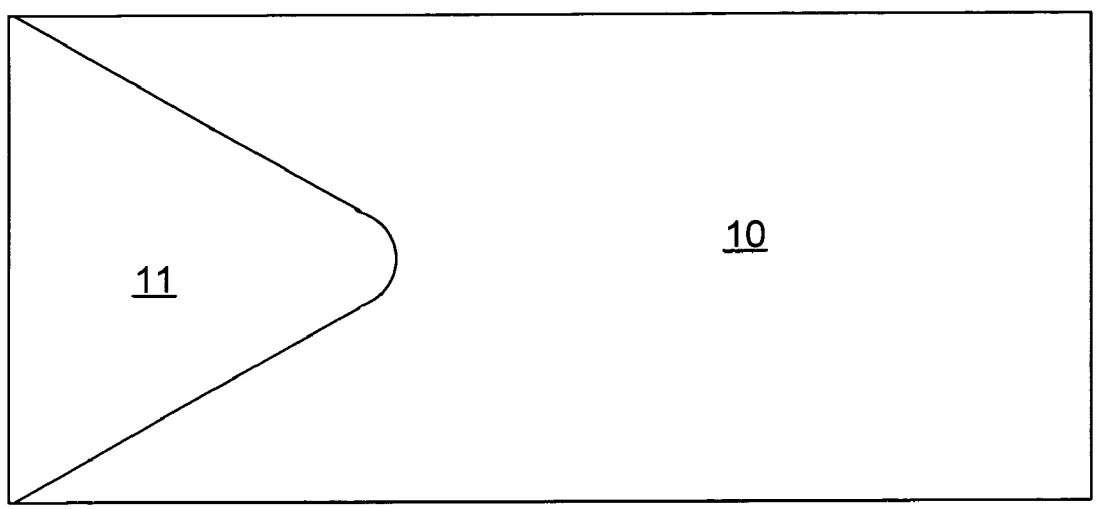
FIG. 1 is an outside perspective view of a waist garment worn around the mid section of the body.

FIG. 1 is an outside perspective view of Waist Garment.

A garment to secure retail and/or medical absorption pads for, but not limited to, post tumescent liposuction. This fabric is the body of the garment. Constructed of, but not limited to, Darlexx 3 Ply Fabric 3645 or other stretchable fabric 10. Velcro Loop 11 or loop type material assists in adjusting the size and securing the waist garment when closed.

Figure 2:
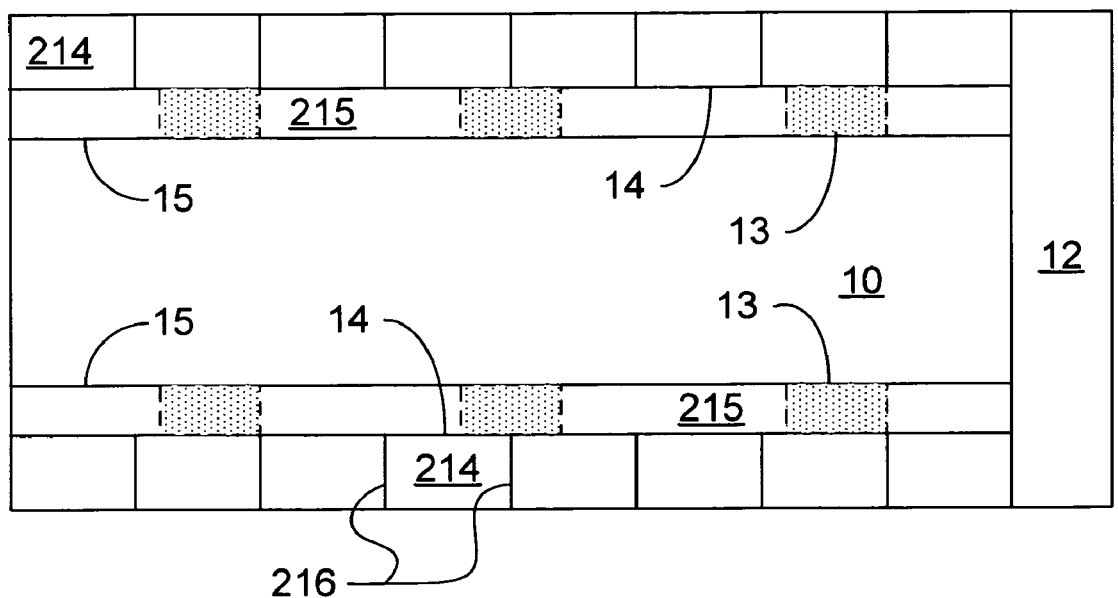
FIG. 2 is an inside perspective view of a waist garment with pockets to secure absorption pads.

FIG. 2 is an inside perspective view of a Waist Garment.

The inside perspective view of the waist garment with pockets allows the patient a choice to use either individual Maxi Pads 17/medical pads or a Large Flat Medical Pad 19. The patient could also choose to use both Maxi Pads 17 and the Large Flat Medical Pad 19 at the same time, giving the patient even more absorption protection. This pocket system allows for ease of placement for these pads. The Velcro Hook 12, which will attach to the Velcro Loop 11, allows the patient ease of size adjustment and comfort. The Elongated Single Pocket 15 made from the same Darlexx 3 Ply Fabric 3645 or other stretchable fabric 10 will allow the patient to customize and place a long flat medical pad within the Elongated Single Pocket 15. The Hook Velcro Strips 13 that are stitched on the underside of the Elongated Single Pocket 15 and spaced accordingly, will further secure the flat medical pad by allowing the hook to embed into the pad's surface. The patient can now easily wrap the garment, once loaded with the pad/s, around the fluid drainage area without concern of the pad/s falling out. The Inside View of the Waist Garment also contains Individual Pad Pockets 14. These Individual Pad Pockets 14 allow for placement of Maxi Pads 17 or retail pads. Using Maxi or retail pads is both convenient and economical, allowing the person to replace only the saturated Maxi Pads 17 or retail pad with a new one when necessary.

Figure 3:
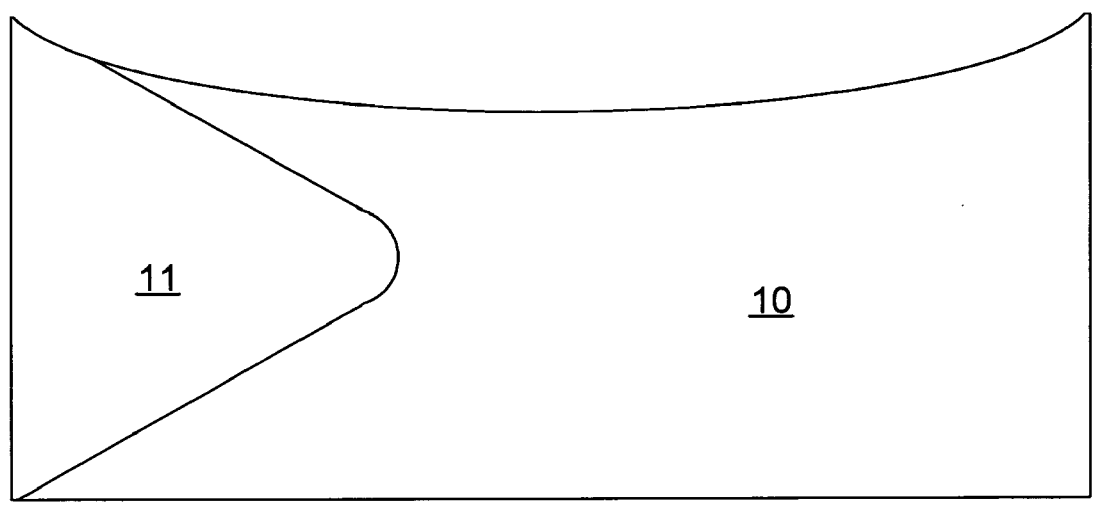
FIG. 3 is an outside perspective view of a leg garment.

FIG. 3 is an outside perspective view of the Leg Garment.

Referencing FIG. 1, made of the same Darlexx 3 Ply Fabric 3645 or other stretchable fabric 10 Velcro Loop 11 that will allow ease of adjustment and comfort.

Figure 4:
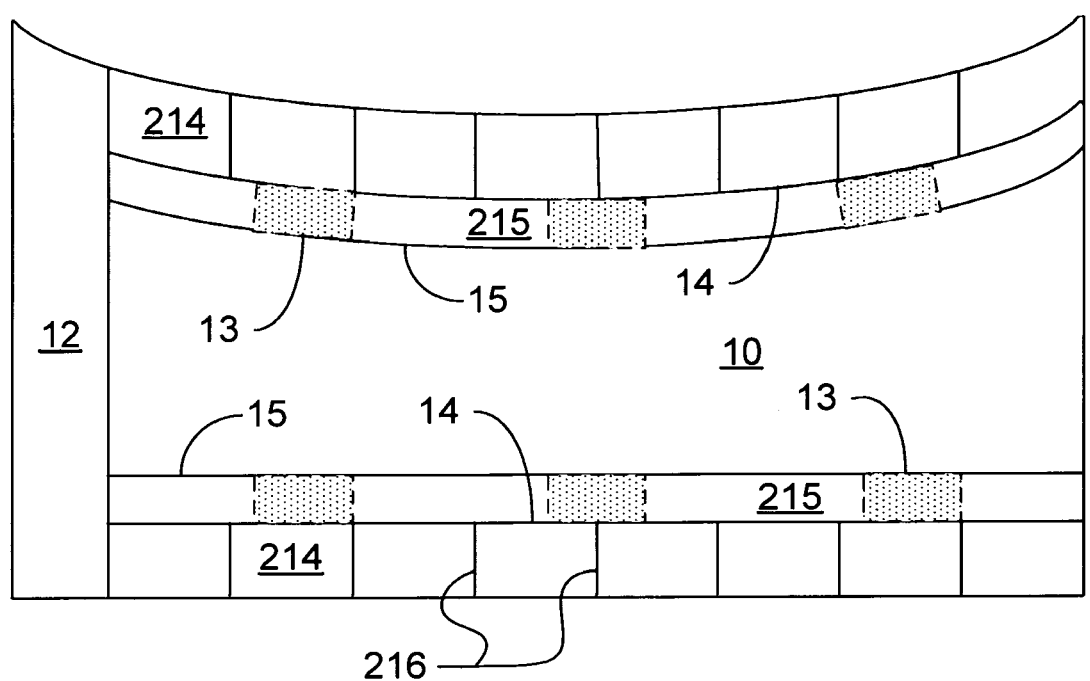
FIG. 4 is an inside perspective view of a leg garment with pockets to secure absorption pads this will allow ease of use.

FIG. 4 is an inside perspective view of a Leg Garment with pocket to secure absorption pads, allowing ease of use. Referencing FIG. 2 as to Velcro Hook 12, Elongated Single Pocket 15, Individual Pad Pockets 14 and Hook Velcro Strips 13. The shape of the garment will fit comfortably around the upper thigh area.

Figure 5:
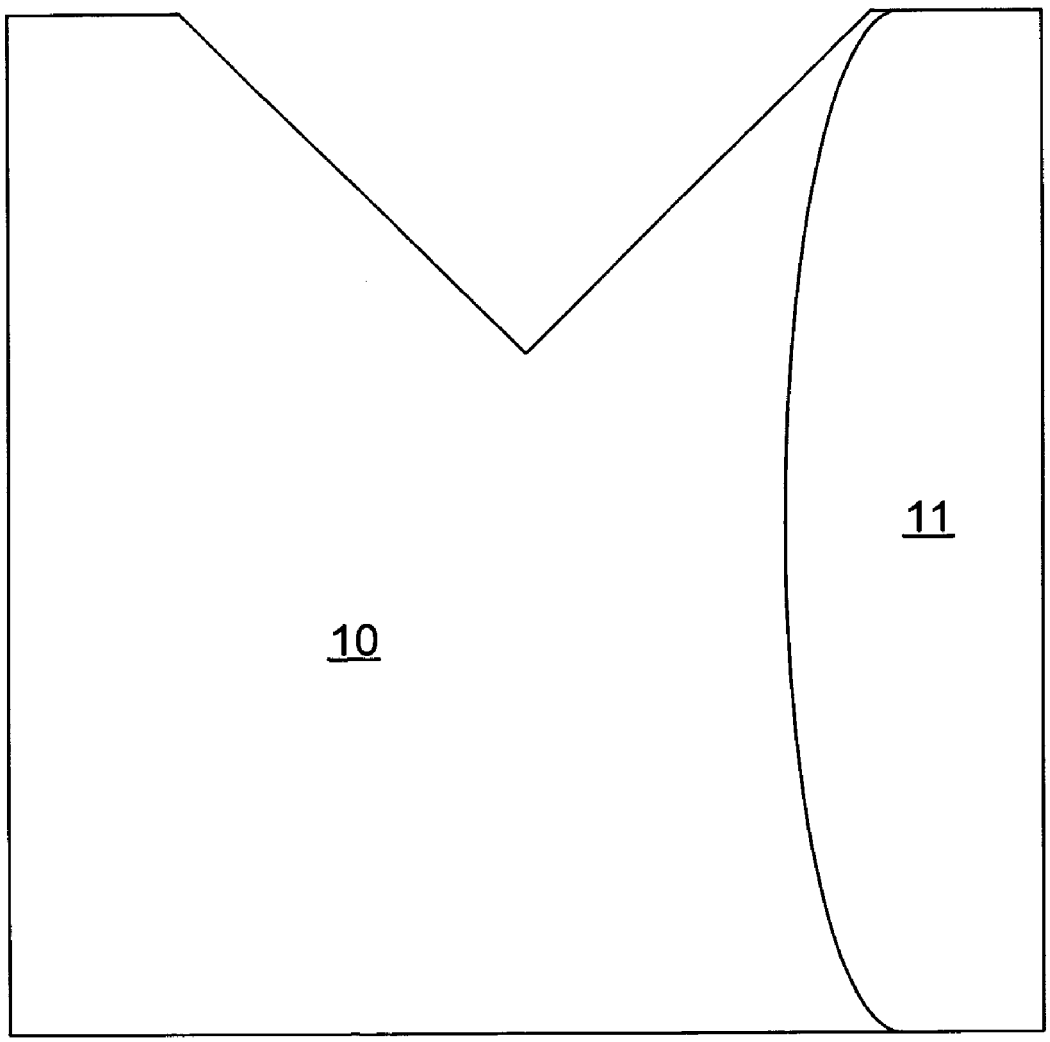
FIG. 5 is an outside perspective view of an arm garment.

FIG. 5 is an outside perspective view of an Arm Garment.

This garment will fit comfortably and will address the tumescent liposuction drainage sites of the upper arm.

Referencing FIG. 1 Darlexx 3 Ply Fabric 3645 or other stretchable fabric 10 and using Velcro Loop 11 fabric for ease and adjustment of closure.

Figure 6:
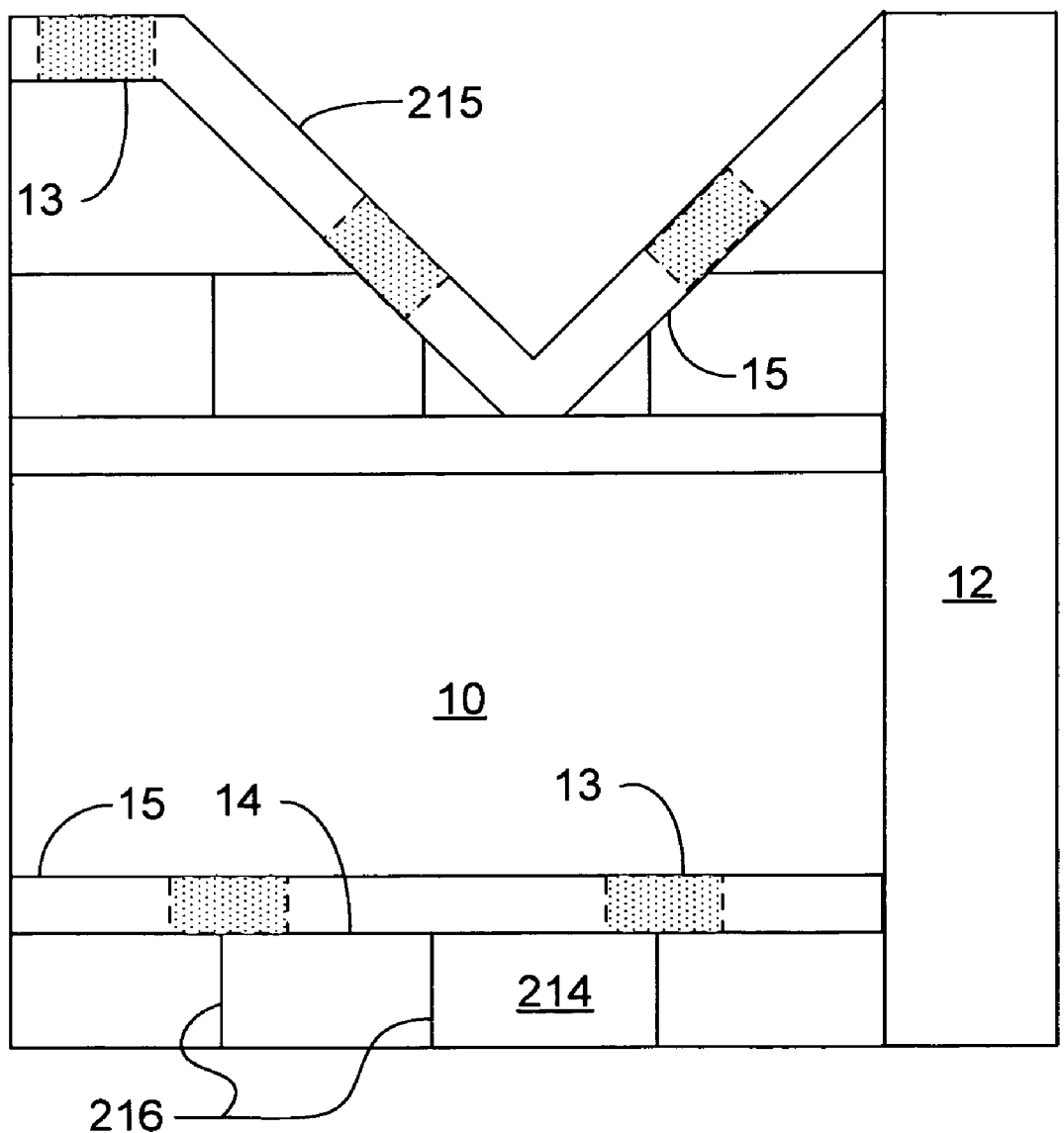
FIG. 6 is an inside perspective view of an arm garment with pockets to secure absorption pads.

FIG. 6 is an inside perspective view of an Arm Garment with pockets to secure absorption pads.

Referencing FIG. 2 using elements Velcro Hook 12, Elongated Single Pocket 15, Individual Pad Pockets 14 and Hook Velcro Strips 13.

Figure 7:
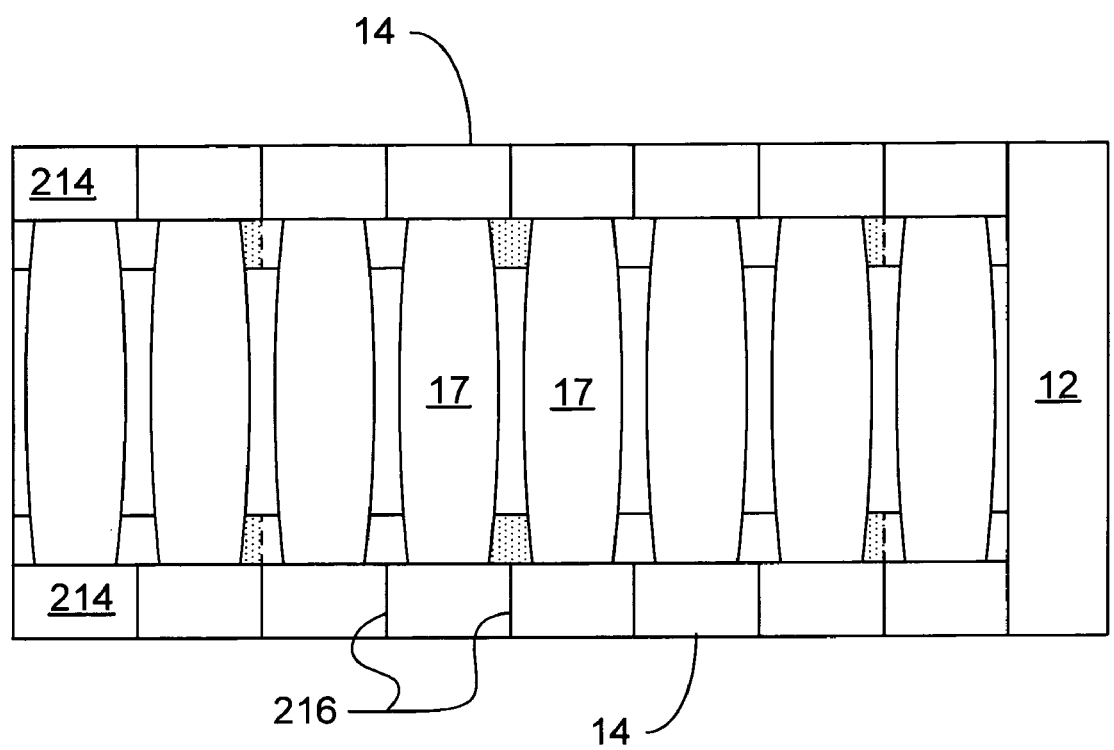
FIG. 7 is an inside perspective view with maxi pads view of an Inside Perspective View With Maxi Pads This is a view of the waist garment filled with Maxi Pads.

FIG. 7 is an inside perspective view of the waist garment loaded with Maxi Pads 17. The view shows how easily the patient can remove and replace using the individual pad pockets 14 as a guide for placement.

Figure 8:
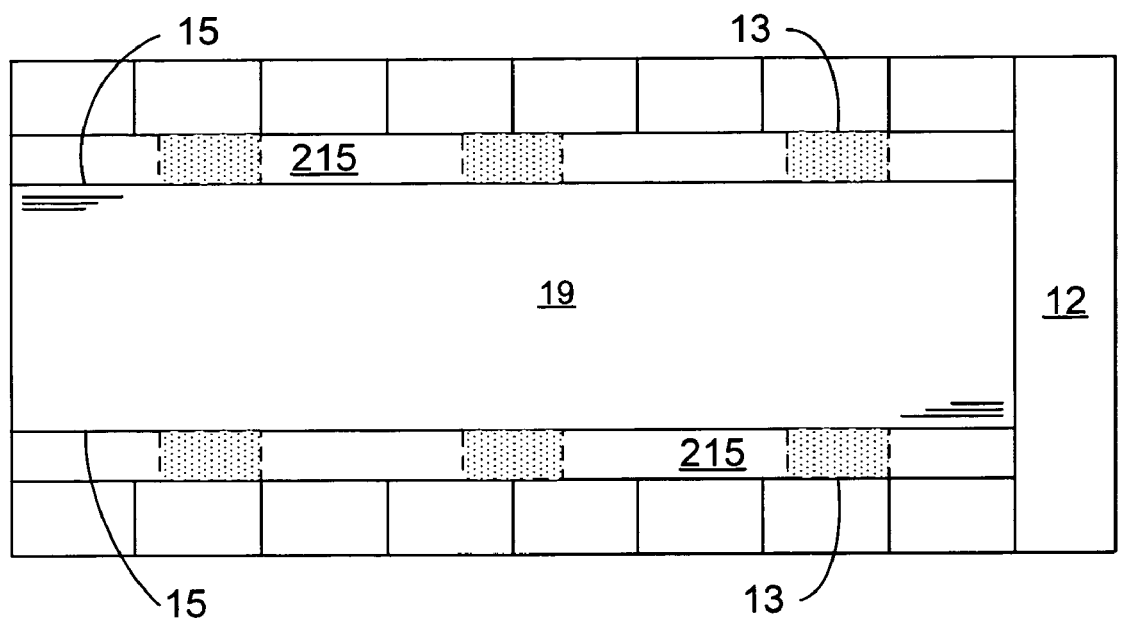
FIG. 8 is an inside perspective view with flat medical pad view of an inside perspective view with flat medical pad waist Garment loaded with a large flat medical pad.

FIG. 8 is an inside perspective view of the waist garment loaded with a Large Flat Medical Pad 19. Using the 2 Elongated Single Pocket 15 for placement and Hook Velcro Strips 13 for security.

FIG. 1 illustrates the outside surface of a garment adapted to wrap around a person's waist. The loop portion 11 of a hook-and-loop fastener system is positioned on the fabric body 10 of the garment. One such hook-and-loop fastener system is known by the trademark Velcro, which is a two part fastener system. Velcro has one part that includes a multitude of resilient hooks attached to a fabric or other material. The hooks engage the other part, which includes a multitude of resilient loops attached to a fabric or other material. In the illustrated embodiment, the waist garment is rectangular with two short ends and two long sides, or long edges. The loop portion 11 is positioned adjacent to one end of the garment such that when the garment is wrapped around a waist of a person, the other end overlaps the loop portion 11.

The fabric body 10 is a stretchable fabric, such as Darlexx 3645. Darlexx is a trademark for a fabric that is breathable, windproof, waterproof, and stretchable with recovery to its original shape. Darlexx fabric is an omni-directional warp knit fabric laminated to a monolithic film.

FIG. 2 illustrates the reverse side of the waist garment illustrated in FIG. 1. The end of the garment opposite the end with the loop portion 11 includes the hook portion 12 of the hook-and-loop fastener system. In the illustrated embodiment, the hook portion 12 is rectangular and is adapted to mate with the loop portion 11 on the opposite surface of the garment when the garment is wrapped around a body portion of the person. The shape and configuration of the loop portion 11 is such that the hook portion 12 mates with the loop portion 11 at various positions, allowing the garment to fit various waist diameters.

Illustrated in FIG. 2 are two strips 215 of fabric and each strip 215 is positioned along the long edges of the garment. The strips 215 are attached to the garment near the edges of the garment such that the strips 215, in combination with the fabric body 10, form a pair of elongated pockets 15 that extend substantially the length of the fabric body 10 along the two edges. Inside the pockets 15 at spaced intervals are strips of hook material 13, such as the hook portion of a Velcro fastening system. The pair of elongated pockets 15 are adapted to receive a flat absorbent medical pad 19, such as illustrated in FIG. 8.

Attached to each of the two first strips 215 is a second strip 214 of fabric. The second strip 214 is attached to the first strip 215 along the seams 216 that are at spaced intervals and parallel to the ends of the garment. The volume bounded by the first strip 215 and the second strip 214 and between two adjacent seams 216 define an individual pad pocket, or restraining member, 14. Each pad pocket 14 has a corresponding pad pocket 14 at the opposite side of the garment such that the ends of an oblong absorbent pad 17 (illustrated in FIG. 7) fit into a pair of opposing pad pockets 14, thereby being secured to the garment.

FIG. 3 illustrates the outside surface of another embodiment of the garment, which is adapted to be wrapped around a person's leg. FIG. 4 illustrates the inside surface of the garment. One skilled in the art will recognize that the loop portion 11 can be located at either end of the garment provided that the hook portion 12 is located on the opposite surface at the opposite end from the loop portion 11 without departing from the spirit and scope of the present invention. Opposite one side of the garment is an edge that curves inward in the mid-section of the garment. The shape of the curved side is such that the garment is adapted to fit around a person's upper thigh.

FIGS. 5 and 6 illustrate the outside and inside surfaces, respectively, of another embodiment of the garment, which is adapted to be wrapped around a person's arm. As shown in FIG. 3, the loop portion 11 illustrated in FIG. 5 is shown positioned on one end of the garment. Opposite one edge of the garment is an edge that has a V-shape pointing inward to the mid-section of the garment. The shape of the V-shaped side is such that the garment is adapted to fit around a person's upper arm.

FIG. 7 illustrates the garment with the ends of the absorbent pads 17 inserted into the pad pockets 14. The absorbent pads 17 are feminine hygiene pads such as Maxi-Pads, which are trademarked pads sold under the trademark Kotex. Such pads are generally rectangular with rounded corners, or oblong, are absorbent of bodily fluids and minimize leakage of the absorbed fluid.

FIG. 8 illustrates the garment shown in FIG. 7 with the oblong absorbent pads 17 removed, exposing the flat medical pad 19. The opposite ends of the flat medical pad 19 are inserted in the pair of elongated pockets 15 and the hook portion 13 inside the elongated pockets 15 are attached to the pad 19, thereby securing the pad 19 to the garment.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A garment for securing absorptive pads for collection of post-tumescent liposuction drainage fluid from a person, said garment comprising:
    a garment body having an outside surface and an inside surface, said garment body having a first end and a second end opposite said first end, said garment having a first edge and a second edge opposite said first edge, said first and second edges extending between said first and second ends;
    a first half of a hook and loop fastener secured adjacent to said first end of said outside surface of said garment body;
    a second half of said hook and loop fastener secured adjacent to said second end of said garment on said inside surface, said second half dimensioned and configured to engage said first half of said hook and loop fastener and form a connection between said first end and said second end of said garment body;
    a pair of opposing first pockets formed on said inside surface of said garment body, a first one of said pair of opposing first pockets adjacent said first edge of said garment body, a second one of said pair of opposing first pockets adjacent said second edge, said pair of opposing first pockets dimensioned and configured to receive a first absorptive pad that extends substantially from said first edge to said second edge of said garment body; and
    a plurality of opposing second pockets formed adjacent said pair of opposing first pockets, each one of a pair of said plurality of opposing second pockets dimensioned and configured to receive an end of an oblong pad whereby said first absorptive pad is sandwiched between said oblong pad and said garment body, said oblong pad being absorptive of bodily fluids.

2. The garment of claim 1 further including a plurality of hook portion members secured to an inside surface of said pair of opposing first pockets, said plurality of hook portion members dimensioned and configured to engage the first absorptive pad when the first absorptive pad is received by said pair of opposing first pockets.

3. The garment of claim 1 wherein said garment is dimensioned and configured to be wrapped around a torso of a person.

4. The garment of claim 1 wherein said first edge has an arcuate shape with said arcuate shape causing said garment body to be narrow near a midsection between said first and second ends, said garment dimensioned and configured to be wrapped around a leg of a person with said first edge adjacent a crotch of the person.

5. The garment of claim 1 wherein said first edge has a V-shape, said garment dimensioned and configured to be wrapped around an arm of a person with said first edge adjacent a shoulder of the person.

6. The garment of claim 1 wherein said garment body includes a stretchable fabric.

7. The garment of claim 1 wherein said garment body includes a stretchable fabric that is breathable.

8. A garment for securing absorptive pads for collection of post-tumescent liposuction drainage fluid from a person, said garment comprising:
    a garment body having an outside surface and an inside surface, said garment body having a first end and a second end opposite said first end, said garment having a first edge and a second edge opposite said first edge, said first and second edges extending between said first and second ends;
    a means for detachably connecting said first end of said garment body to said second end of said garment body;
    a first strip of fabric attached to said garment body adjacent to said first edge of said garment body, said first strip and said garment body defining a first pocket;
    a second strip of fabric attached to said garment body adjacent to said second edge of said garment body, said second strip and said garment body defining a second pocket, said first pocket having an opening opposite an opening of said second pocket, said first and second pockets dimensioned and configured to receive a first pad that is absorbent;
    a third strip of fabric attached to said first strip of fabric at spaced intervals, said third strip of fabric and said first strip of fabric defining a plurality of first openings, each one of said plurality of first openings for receiving a first end of an oblong pad; and
    a fourth strip of fabric attached to a said second strip of fabric at spaced intervals, said fourth strip of fabric and said second strip of fabric defining a plurality of second openings, each one of said plurality of second openings for receiving a second end of the oblong pad.

9. The garment of claim 8 wherein said means for detachably connecting includes a first half of a hook and loop fastener secured adjacent to said first end of said outside surface of said garment body, and a second half of said hook and loop fastener secured adjacent to said second end of said garment on said inside surface, said second half dimensioned and configured to engage said first half of said hook and loop fastener and form a connection between said first end and said second end of said garment body.

10. The garment of claim 8 wherein said garment is dimensioned and configured to be wrapped around a torso of a person.

11. The garment of claim 8 wherein said first edge has an arcuate shape with said arcuate shape causing said garment body to be narrow near a midsection between said first and second ends, said garment dimensioned and configured to be wrapped around a leg of a person with said first edge adjacent a crotch of the person.

12. The garment of claim 8 wherein said first edge has a V-shape, said garment dimensioned and configured to be wrapped around an arm of a person with said first edge adjacent a shoulder of the person.

13. The garment of claim 8 wherein said garment body includes a stretchable fabric.

14. The garment of claim 8 wherein said garment body includes a stretchable fabric that is breathable.

15. A garment for removably securing absorptive pads for collection of post-tumescent liposuction drainage fluid from a person, said garment comprising:
- a garment body having an outside surface and an inside surface, said garment body having a first end and a second end opposite said first end, said garment having a first edge and a second edge opposite said first edge, said first and second edges extending between said first and second ends;
- a means for detachably connecting said first end of said garment body to said second end of said garment body;
- a first pocket located adjacent said first edge of said garment body;
- a second pocket located adjacent said second edge, said first pocket having an opening facing an opening of said second pocket, each of said first and second pockets dimensioned and configured to receive one end of a first adsorptive pad;
- at least one third pocket located adjacent said first pocket, said at least one third pocket receiving a first end of an oblong pad, the oblong pad being absorptive of bodily fluids; and
- at least one fourth pocket located adjacent said second pocket, said at least one fourth pocket receiving a second end of the oblong pad.

16. The garment of claim 15 wherein said means for detachably connecting includes a first half of a hook and loop fastener secured adjacent to said first end of said outside surface of said garment body, and a second half of said hook and loop fastener secured adjacent to said second end of said garment on said inside surface, said second half dimensioned and configured to engage said first half of said hook and loop fastener and form a connection between said first end and said second end of said garment body.

17. The garment of claim 15 wherein said garment is dimensioned and configured to be wrapped around a torso of a person.

18. The garment of claim 15 wherein said first edge has an arcuate shape with said arcuate shape causing said garment body to be narrow near a midsection between said first and second ends, said garment dimensioned and configured to be wrapped around a leg of a person with said first edge adjacent a crotch of the person.

19. The garment of claim 15 wherein said first edge has a V-shape, said garment dimensioned and configured to be wrapped around an arm of a person with said first edge adjacent a shoulder of the person.

* * * * *